United States Patent

Hoehn

[11] 4,153,796
[45] May 8, 1979

[54] HYDRAZINO DERIVATIVES OF 1H-PYRAZOLO(3,4-B)-PYRIDINE-5-CARBOXAMIDES

[75] Inventor: Hans Hoehn, Tegernheim, Fed. Rep. of Germany

[73] Assignee: E. R. Squibb & Sons, Inc., Princeton, N.J.

[21] Appl. No.: 923,128

[22] Filed: Jul. 10, 1978

[51] Int. Cl.$^2$ .................................. C07D 471/04
[52] U.S. Cl. ............................ 546/120; 424/256
[58] Field of Search .......................... 546/120

[56] References Cited

U.S. PATENT DOCUMENTS

| | | | |
|---|---|---|---|
| 3,761,487 | 9/1973 | Hoehn et al. | 260/295.5 B |
| 3,810,905 | 5/1974 | Hoehn et al. | 260/295.5 B |
| 3,840,546 | 10/1974 | Hoehn et al. | 260/295.5 B |
| 3,849,411 | 11/1974 | Hoehn et al. | 546/120 |
| 3,979,399 | 9/1976 | Hoehn et al. | 546/120 |
| 3,984,422 | 10/1976 | Denzel et al. | 546/120 |
| 4,020,072 | 4/1977 | Hoehn | 546/120 |
| 4,038,281 | 7/1977 | Denzel et al. | 546/120 |

*Primary Examiner*—Alan L. Rotman
*Attorney, Agent, or Firm*—Lawrence S. Levinson; Merle J. Smith

[57] ABSTRACT

Hydrazino derivatives of 1H-pyrazolo[3,4-b]-pyridine-5-carboxamides which have the general formula

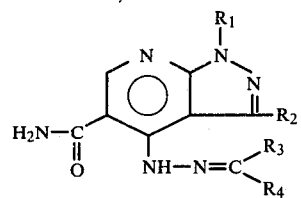

are useful as ataractic agents, anti-allergy agents or anti-bronchoconstrictor agents.

8 Claims, No Drawings

HYDRAZINO DERIVATIVES OF 1H-PYRAZOLO(3,4-B)-PYRIDINE-5-CARBOXAMIDES

SUMMARY OF THE INVENTION

This invention relates to new compounds which have the formula

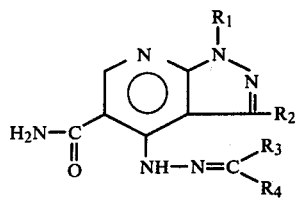

wherein
$R_1$ is hydrogen, lower alkyl or phenyl-lower alkyl;
$R_2$ and $R_3$ each is hydrogen or lower alkyl; and
$R_4$ is lower alkyl
and to intermediates therefor which have the formula

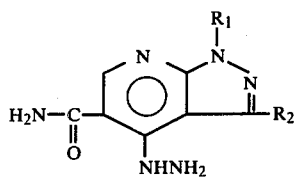

wherein $R_1$ and $R_2$ have the same meaning as above.

DETAILED DESCRIPTION OF THE INVENTION

The lower alkyl groups include the $C_1$-$C_7$ straight and branched chain aliphatic hydrocarbon radicals like methyl, ethyl, propyl, isopropyl, butyl, isobutyl, t-butyl, pentyl, hexyl, heptyl and the like. The $C_1$-$C_4$ members, and especially the $C_1$-$C_2$ members, are preferred. The phenyl-lower alkyl groups include a phenyl ring attached to an alkyl group like those referred to above. Those with $C_1$-$C_4$ alkyl groups and especially phenylmethyl and phenylethyl, are preferred.

Preferred are those compounds of formulas I and II wherein $R_1$, $R_3$ and $R_4$ each is lower alkyl, especially methyl and ethyl, and $R_2$ is hydrogen.

The compounds of this invention can be produced by either of two methods. According to one method, a 4-lower alkoxy-1H-pyrazolo[3,4-b]-pyridine-5-carboxamide which has the formula

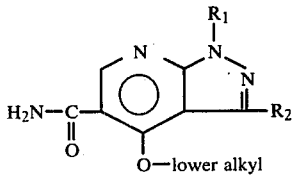

[produced by the method described in J. Het. Chem. 9, 235 (1972); see Procedure S (page 252) as well as Table VII (page 247) See also U.S. Pat. No. 3,810,905] is made to react with hydrazine or its hydrate in an inert organic solvent like methanol. This yields the intermediate which has the formula II above. Treatment of this intermediate with an aldehyde $R_3$—CHO or ketone

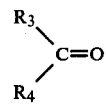

yields the hydrazone of formula I.

According to an alternate method, a compound which has the formula

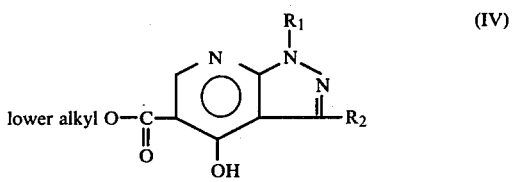

(produced by the method described in the U.S. Pat. referred to above or U.S. Pat. No. 3,761,487) is converted with ammonia, e.g., by heating in a solvent such as dimethylformamide, to the amide which has the formula

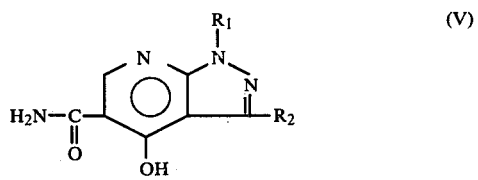

Heating the product of formula V with a thionyl halide, preferably the chloride, yields the halogenated nitrile which has the formula

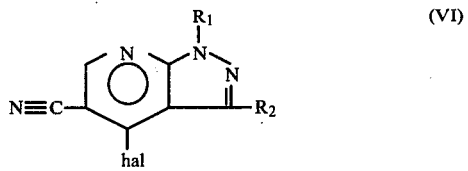

wherein hal represents halogen. Treatment of the halogenated nitrile with a concentrated strong mineral acid like sulfuric acid yields a halogenated amide which has the formula

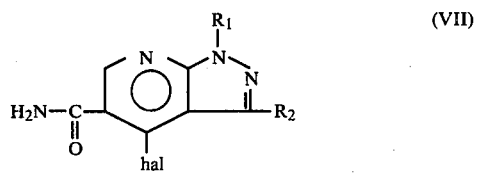

Reaction of this product with hydrazine or its hydrate, as described above, yields the same intermediate of formula II above, which can then be converted with aldehyde or ketone to the desired end product.

Additional illustrative reaction particulars are provided in the examples.

The new compounds of this invention are mild central nervous system depressants and may be used as tranquilizers or ataractic agents for the relief of anxiety and tension states, for example, in mice, cats, rats, dogs and other mammalian species, in the same manner as chlordiazepoxide. For this purpose a compound or mixture of compounds of formula I, is preferably administered orally, but parenteral routes such as subcutaneously, intramuscularly, intravenously or intraperitoneally, in the described dosages, can also be employed. A single dose, or preferably 2 to 4 divided daily doses, provided on a basis of about 5 to 200mg. per kilogram per day, preferably about 10 to 15 mg. per kilogram per day, is appropriate. These may be conventionally formulated in an oral or parenteral dosage form by compounding about 100 to 500mg. per unit of dosage with conventional vehicle, excipient, binder, preservative, stabilizer, flavor or the like according to accepted pharmaceutical practice.

The compounds of this invention also have antiallergy activity. They inhibit the effects of certain antigen-antibody reactions and, in particular, inhibit the release of mediators such as histamine. The activity of these compounds is demonstrated by the reaginic antibody induced passive cutaneous anaphylaxis (PCA) reaction in rats. [See Bach, Immediate Hypersensitivity: Laboratory Models and Experimental Findings, Ann. .Rep. Med. Chem. 7, 238-248 (1972)]. These compounds also show anti-bronchoconstrictor activity without marked concomitant cardiovascular effects as shown in histamine induced bronchospasm in pithed guinea pigs.

The compounds of formula I are therefore useful in treating various allergic conditions in mammalian species such as mice, cats, dogs, etc., when administered in amounts ranging from about 0.3 to about 300 milligrams per kilogram per day. The compounds can be used to alleviate or relieve various allergic disorders and in particular to treat certain types of asthma, hay-fever, rhinitis and/or other conditions involving bronchoconstriction. A preferred dosage is about 3 milligrams to about 100 milligrams per kilogram per day administered in a single dose or two to four divided doses.

A compound of formula I can be administered by the inhalation of an aerosol or powder as described in U.S. Pat. No. 3,772,336 (i.e., breathing finely divided particles of the active ingredient into the lungs), or orally or parenterally. Powders can be prepared by comminuting the active ingredient with a similarly comminuted diluent such as starch or lactose. Suitable forms for oral administration include capsules, tablets, and syrups, and a suitable form for parenteral administration is a sterile injectable. Such unit dosage forms are prepared by compounding with a conventional vehicle, excipients, binders, preservatives, stabilizers, flavoring agents or the like as called for by acceptable pharmaceutical practice.

For oral administration, for example, the active substance can be combined with an inert diluent or with an assimilable edible carrier or it can be enclosed in hard or soft gelatin capsules or compressed into tablets. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a dosage as described above is obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following examples further illustrate and represent preferred embodiments of the invention. All temperatures are expressed in degrees Celsius.

EXAMPLE 1

1-Ethyl-4-hydrazino-1H-pyrazolo[3,4-b]pyridine-5-carboxamide

To 3.6 g. of 4-ethoxy-1-ethyl-1H-pyrazolo-[3,4-b]pyridine-5-carboxamide [J. Het. Chem. 9, 235 (1972)] (0.0154 mol.), dissolved in 100 ml. of hot methanol, are added 0.83g. of hydrazine hydrate (98%). On allowing the reaction mixture to stand for 3 days, 2.15g. of 1-ethyl-4-hydrazino-1H-pyrazolo[3,4-b]pyridine-5-carboxamide crystallize out. Work up of the mother liquor gives another 0.9g., total yield 3.05g. (90%). The product is recrystallized from ethanol, m.p. 201°-202° (dec.).

EXAMPLE 2

1-Ethyl-4-[2-(1-methylethylidene)hydrazino]-1H-pyrazolo[3,4-b]pyridine-5-carboxamide 14 g. of well pulverized 1-ethyl-4-hydrazino-1H-pyrazolo[3,4-b]pyridine-5-carboxamide (0.0635 mol.) are dissolved in 500ml. of anhydrous acetone and the solution is allowed to stand overnight. Then excess acetone is removed in vacuo and the residual 1-ethyl-4-[2-(1-methylethylidene)hydrazino]-1H-pyrazolo[3,4-b]pyridine-5-carboxamide is recrystallized from ethyl acetate, m.p. 217°-218°, yield 9.75 g. (59%).

EXAMPLE 3

(a)

1-Ethyl-4-hydroxy-1H-pyrazolo[3,4-b]pyridine-5-carboxamide.

6.8 g. of ethyl-1-ethyl-4-hydroxy-1H-pyrazolo-[3,4-b]pyridine-5-carboxylate (J. Het. Chem., supra) (0.029 mol.) and 100 ml. of ammonia in dimethylformamide (48 g. $NH_3$/1; cooled at 4°) are filled into a steel autoclave. The mixture is heated to 150° for 6 hours. After cooling, the solution is evaporated to dryness and the residue is treated with ether. The 1-ethyl-4-hydroxy-1H-pyrazolo[3,4-b]pyridine-5-carboxamide is used in the next step without further purification. A sample, recrystallized from ethanol, melts at 267°-268° (dec.), yield 3.6 g. (60%).

(b)

4-Chloro-1-ethyl-1H-pyrazolo[3,4-b]pyridine-5-carbonitrile 10.3 g. of 1-ethyl-4-hydroxy-1H-pyrazolo-[3,4-b]pyridine-5-carboxamide (0.05 mol.) and 125ml. of thionyl chloride are refluxed for 3.5 hours. After cooling, the thionyl chloride is removed in vacuo and the residue is extracted twice with 400ml. of refluxing hexane. The combined extracts are treated with charcoal, filtered and evaporated. The product, 4-chloro-1-ethyl-1H-pyrazolo[3,4-b]pyridine-5-carbonitrile, is recrystallized from a small amount of hexane, yield 2.9 g. (28%), m.p. 100°-102°.

(c)

4-Chloro-1ethyl-1H-pyrazolo[3,4-b]pyridine-5-carboxamide 4.25 g. of 4-chloro-1-ethyl-1H-pyrazolo[3,4-b]-pyridine-5-carbonitrile (0.02 mol.) are added to 21 ml. of concentrated sulfuric acid. The mixture is stirred at room temperature for 3 days. Then 200 ml. of ice-water are introduced, while cooling with ice-water, and the mixture is allowed to stand overnight in a refrigerator. 2.04 g. (46%) of pure 4-chloro-1-ethyl-1H-pyrazolo[3,4-b]-pyridine-5-carboxamide are obtained, m.p. 192°-193°.

(d)

1-Ethyl-4-hydrazino-1H-pyrazolo[3,4-b]pyridine-5-carboxamide

To 1 g. of 4-chloro-1-ethyl-1H-pyrazolo-[3,4-b]pyridine-5-carboxamide (0.0044 mol.), dissolved in 100 ml. of absolute ethanol, are added 0.4 ml. of hydrazine hydrate 98% (0.008 mol.). The mixture is allowed to stand for 24 hours. Evaporation of the solution to a fourth of its volume yields 0.7 g. (73%) of 1-ethyl-4-hydrazino-1H-pyrazolo-[3,4-b]pyridine-5-carboxamide, m.p. 197°-199°. Recrystallization from ethanol elevates the melting point to 201°-202° (dec.).

EXAMPLE 4

1-Ethyl-4-[2-(1-methylethylidene)hydrazino]-1H-pyrazolo[3,4-b]pyridine-5-carboxamide The product of Example 3d is treated with acetone according to the procedure of Example 2 to obtain 1-ethyl-4-[2-(methylethylidene)hydrazino]-1H-pyrazolo[3,4-b]pyridine-5-carboxamide.

The following additional intermediates (A) and final products (B) are obtained by the procedure of Examples 1 and 2 by substituting for the 4-ethoxy-1-ethyl-1H-pyrazolo[3,4-b]pyridine-5-carboxamide, the 4-ethoxy-1H-pyrazolo[3,4-b]pyridine-5-carboxamide having the substituents in the 1- and 2- positions ($R_1$, $R_2$) in the following table, and by substituting for the acetone the aldehyde or ketone having the substituents $R_3$ and $R_4$ in the table:

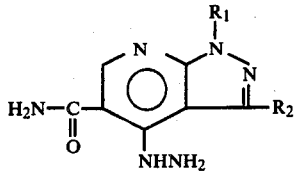

A

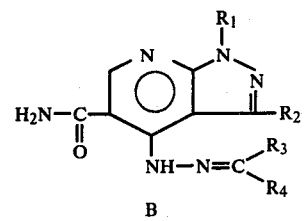

B

| Example | $R_1$ | $R_2$ | $R_3$ | $R_4$ |
| --- | --- | --- | --- | --- |
| 5 | H | H | H | $CH_3$ |
| 6 | $C_3H_7$ | H | $CH_3$ | $CH_3$ |
| 7 | $C_4H_9$ | $CH_3$ | $CH_3$ | $CH_3$ |
| 8 | $C_2H_5$ | $CH_3$ | H | $C_2H_5$ |
| 9 | H | H | $CH_3$ | $CH_3$ |
| 10 | $CH_3$ | H | $C_2H_5$ | $C_2H_5$ |
| 11 | $C_2H_5$ | H | H | $C_4H_9$ |
| 12 | $C_6H_5CH_2-$ | H | $CH_3$ | $CH_3$ |
| 13 | $C_2H_5$ | $C_3H_7$ | $CH_3$ | $C_2H_5$ |
| 14 | $C_6H_5CH_2CH_2-$ | H | $CH_3$ | $CH_3$ |
| 15 | $C_2H_5$ | $C_4H_9$ | H | $C_2H_5$ |

What is claimed is:

1. A compound of the formula

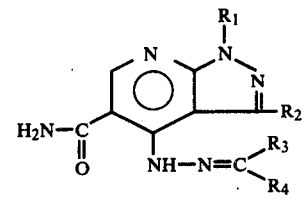

wherein
$R_1$ is hydrogen, lower alkyl or phenyl-lower alkyl;
$R_2$ and $R_3$ each is hydrogen or lower alkyl; and
$R_4$ is lower alkyl.

2. A compound as in claim 1 wherein $R_1$, $R_3$ and $R_4$ each is lower alkyl and $R_2$ is hydrogen.

3. A compound as in claim 1 wherein $R_2$ is hydrogen.

4. A compound as in claim 1 wherein $R_1$ is ethyl; $R_2$ is hydrogen; and $R_3$ and $R_4$ each is methyl.

5. A compound of the formula

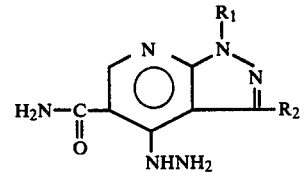

wherein
$R_1$ and $R_2$ have the same meaning as in claim 1.

6. A compound as in claim 5 wherein $R_1$ is lower alkyl and $R_2$ is hydrogen.

7. A compound as in claim 6 wherein $R_2$ is hydrogen.

8. A compound as in claim 6 wherein the lower alkyl group is ethyl.

* * * * *